United States Patent
Mattsson

(10) Patent No.: US 7,105,163 B1
(45) Date of Patent: Sep. 12, 2006

(54) MITE PROTEIN

(75) Inventor: Jens Mattsson, Uppsala (SE)

(73) Assignee: Statens Veterinarmedicinska Anstalt, Uppsala (SE)

( * ) Notice: Subject to any disclaimer, the term of this patent is extended or adjusted under 35 U.S.C. 154(b) by 0 days.

(21) Appl. No.: 09/914,352

(22) PCT Filed: Feb. 22, 2000

(86) PCT No.: PCT/SE00/00346

§ 371 (c)(1),
(2), (4) Date: Dec. 14, 2001

(87) PCT Pub. No.: WO00/50450

PCT Pub. Date: Aug. 31, 2000

(30) Foreign Application Priority Data

Feb. 25, 1999 (SE) .................................. 9900674

(51) Int. Cl.
*A61K 39/00* (2006.01)
*C07K 14/00* (2006.01)
*C07K 16/00* (2006.01)

(52) U.S. Cl. .................... 424/185.1; 530/300; 530/324

(58) Field of Classification Search ............. 424/184.1, 424/185.1; 435/7.1, 69.1, 252.3, 320.1, 975; 530/300, 350, 387.1, 388.1, 324; 536/23.1
See application file for complete search history.

(56) References Cited

U.S. PATENT DOCUMENTS 5,302,527 A * 4/1994 Birkett et al.

6,171,800 B1 * 1/2001 Hsu

FOREIGN PATENT DOCUMENTS

| EP | 0 473 111 A2 | 8/1991 |
| JP | A 07112999 A | 1/1996 |
| JP | A 08301788 | 3/1997 |

OTHER PUBLICATIONS

Plotkin et al Vaccines WB Saunders Co. Philadelphia, 1988, p. 571.*
Medline accession No. 99113129, Moustafa EH et al, "The Relation Between Scabies and Hypersensitivity to Antigens of House Dust Mites and Storage Mites," *J. Egypt Soc. Parasitol*, v. 28, No. 3, 1998 pp. 777-787.

* cited by examiner

*Primary Examiner*—Mark Navarro
(74) *Attorney, Agent, or Firm*—Young & Thompson

(57) ABSTRACT

The present invention relates to a novel major mite antigen, which according to the invention has been isolated and sequenced for the first time. More specifically, said antigen is a protein originating from the mite *Sarcoptes scabiei*. Thus, the invention relates to said antigen as well as to the encoding nucleic acid as defined in the claims. Further, the invention also relates to advantageous uses of the novel protein and/or functional fragments thereof, e.g. in immunological testing, such as in ELISA methods, as well as in the preparation of vaccines.

3 Claims, 4 Drawing Sheets

The native MSA1 protein

The recombinant MSA1 protein

Continous MSA cDNA fragment, inserted into pPU16.

SEQUENCE LISTING

<160> NUMBER OF SEQ ID NOS: 7

<210> SEQ ID NO 1
<211> LENGTH: 1284
<212> TYPE: DNA
<213> ORGANISM: Sarcoptes scabiei
<220> FEATURE:
<221> NAME/KEY: CDS
<222> LOCATION: (1)..(1281)

<400> SEQUENCE: 1

| gaa | gcg | gaa | gtt | acg | ttc | tcc | gat | agt | gaa | gat | aag | aaa | aat | tat | ttc | 48 |
|---|---|---|---|---|---|---|---|---|---|---|---|---|---|---|---|---|
| Glu | Ala | Glu | Val | Thr | Phe | Ser | Asp | Ser | Glu | Asp | Lys | Lys | Asn | Tyr | Phe | |
| 1 | | | | 5 | | | | | 10 | | | | | 15 | | |

| gtc | gaa | ctt | aaa | aaa | gat | aaa | gat | tta | tat | tcg | atg | aaa | tcg | aat | gtg | 96 |
|---|---|---|---|---|---|---|---|---|---|---|---|---|---|---|---|---|
| Val | Glu | Leu | Lys | Lys | Asp | Lys | Asp | Leu | Tyr | Ser | Met | Lys | Ser | Asn | Val | |
| | | | 20 | | | | | 25 | | | | | 30 | | | |

| aaa | cga | aac | aat | gag | att | ttc | tat | gag | aac | aat | atg | gat | ttg | gag | aag | 144 |
|---|---|---|---|---|---|---|---|---|---|---|---|---|---|---|---|---|
| Lys | Arg | Asn | Asn | Glu | Ile | Phe | Tyr | Glu | Asn | Asn | Met | Asp | Leu | Glu | Lys | |
| | | 35 | | | | | 40 | | | | | 45 | | | | |

| aac | ggt | aaa | atg | aat | tgg | tat | tac | aaa | cga | aac | gat | cga | aca | tgg | aat | 192 |
|---|---|---|---|---|---|---|---|---|---|---|---|---|---|---|---|---|
| Asn | Gly | Lys | Met | Asn | Trp | Tyr | Tyr | Lys | Arg | Asn | Asp | Arg | Thr | Trp | Asn | |
| 50 | | | | | 55 | | | | | 60 | | | | | | |

| atg | gat | ctc | gat | aat | gca | ttc | aat | cca | aga | gat | ggt | aca | atg | aaa | ctt | 240 |
|---|---|---|---|---|---|---|---|---|---|---|---|---|---|---|---|---|
| Met | Asp | Leu | Asp | Asn | Ala | Phe | Asn | Pro | Arg | Asp | Gly | Thr | Met | Lys | Leu | |
| 65 | | | | | 70 | | | | | 75 | | | | | 80 | |

| caa | gtg | aaa | gat | cgt | atc | tat | gat | atc | aaa | ttg | aaa | cga | gaa | cgg | ttc | 288 |
|---|---|---|---|---|---|---|---|---|---|---|---|---|---|---|---|---|
| Gln | Val | Lys | Asp | Arg | Ile | Tyr | Asp | Ile | Lys | Leu | Lys | Arg | Glu | Arg | Phe | |
| | | | | 85 | | | | | 90 | | | | | 95 | | |

| cga | tac | ggt | gat | cta | cat | atc | gaa | gga | aat | gag | aat | cct | ttg | atc | aaa | 336 |
|---|---|---|---|---|---|---|---|---|---|---|---|---|---|---|---|---|
| Arg | Tyr | Gly | Asp | Leu | His | Ile | Glu | Gly | Asn | Glu | Asn | Pro | Leu | Ile | Lys | |
| | | | 100 | | | | | 105 | | | | | 110 | | | |

| aag | ggt | gat | tta | cat | atg | tct | ctc | gtc | gat | ccg | ctt | act | ttg | aat | gtt | 384 |
|---|---|---|---|---|---|---|---|---|---|---|---|---|---|---|---|---|
| Lys | Gly | Asp | Leu | His | Met | Ser | Leu | Val | Asp | Pro | Leu | Thr | Leu | Asn | Val | |
| | | 115 | | | | | 120 | | | | | 125 | | | | |

| ttg | acc | aag | aat | gat | gga | atc | gtc | gat | atg | aca | ttg | gat | ttg | gtc | tct | 432 |
|---|---|---|---|---|---|---|---|---|---|---|---|---|---|---|---|---|
| Leu | Thr | Lys | Asn | Asp | Gly | Ile | Val | Asp | Met | Thr | Leu | Asp | Leu | Val | Ser | |
| | 130 | | | | | 135 | | | | | 140 | | | | | |

| ccc | aac | acc | aaa | aaa | gca | gcg | cta | aaa | atc | aat | tcg | aaa | aaa | tac | gat | 480 |
|---|---|---|---|---|---|---|---|---|---|---|---|---|---|---|---|---|
| Pro | Asn | Thr | Lys | Lys | Ala | Ala | Leu | Lys | Ile | Asn | Ser | Lys | Lys | Tyr | Asp | |
| 145 | | | | | 150 | | | | | 155 | | | | | 160 | |

| ctt | gat | cat | gat | ggt | gag | att | acc | gtt | tcg | atc | ttt | aat | cct | cga | atg | 528 |
|---|---|---|---|---|---|---|---|---|---|---|---|---|---|---|---|---|
| Leu | Asp | His | Asp | Gly | Glu | Ile | Thr | Val | Ser | Ile | Phe | Asn | Pro | Arg | Met | |
| | | | | 165 | | | | | 170 | | | | | 175 | | |

| act | tgg | aaa | cat | cac | act | aga | aaa | ggt | gat | atg | gaa | ttg | aat | att | gat | 576 |
|---|---|---|---|---|---|---|---|---|---|---|---|---|---|---|---|---|
| Thr | Trp | Lys | His | His | Thr | Arg | Lys | Gly | Asp | Met | Glu | Leu | Asn | Ile | Asp | |
| | | | 180 | | | | | 185 | | | | | 190 | | | |

| gct | gat | atc | act | cga | aaa | ggt | tca | ttg | atc | acc | tat | tct | cgt | aaa | gag | 624 |
|---|---|---|---|---|---|---|---|---|---|---|---|---|---|---|---|---|
| Ala | Asp | Ile | Thr | Arg | Lys | Gly | Ser | Leu | Ile | Thr | Tyr | Ser | Arg | Lys | Glu | |
| | | 195 | | | | | 200 | | | | | 205 | | | | |

| cca | gat | gat | tcg | aca | aaa | gtt | cga | tat | tca | aga | caa | gga | aat | caa | gtt | 672 |
|---|---|---|---|---|---|---|---|---|---|---|---|---|---|---|---|---|
| Pro | Asp | Asp | Ser | Thr | Lys | Val | Arg | Tyr | Ser | Arg | Gln | Gly | Asn | Gln | Val | |
| | 210 | | | | | 215 | | | | | 220 | | | | | |

| tcg | atg | gaa | gtc | gat | tct | aaa | ttg | atc | gaa | ggc | cat | gcg | aac | gga | act | 720 |
|---|---|---|---|---|---|---|---|---|---|---|---|---|---|---|---|---|
| Ser | Met | Glu | Val | Asp | Ser | Lys | Leu | Ile | Glu | Gly | His | Ala | Asn | Gly | Thr | |
| 225 | | | | | 230 | | | | | 235 | | | | | 240 | |

| ttg | acc | gat | ggc | aaa | att | cat | gtc | aaa | ggt | cga | gag | agt | gat | ttc | gaa | 768 |
|---|---|---|---|---|---|---|---|---|---|---|---|---|---|---|---|---|
| Leu | Thr | Asp | Gly | Lys | Ile | His | Val | Lys | Gly | Arg | Glu | Ser | Asp | Phe | Glu | |
| | | | | 245 | | | | | 250 | | | | | 255 | | |

-continued

```
atc gaa agc acc tat aaa gtt gaa gat ggt aag ctt atg att gag cca        816
Ile Glu Ser Thr Tyr Lys Val Glu Asp Gly Lys Leu Met Ile Glu Pro
        260                 265                 270 acc aaa act cag aat gga aaa tta gaa ggt ctt ctt tcg aga aaa gta        864
Thr Lys Thr Gln Asn Gly Lys Leu Glu Gly Leu Leu Ser Arg Lys Val
275                 280                 285 cca tca cat ctt gtt ctt gaa aca cca aga gtg aaa atg aac atg aaa        912
Pro Ser His Leu Val Leu Glu Thr Pro Arg Val Lys Met Asn Met Lys
    290                 295                 300 tat gat aga ttt gct ccg gtg aag ata ttg aaa tta gat tac gat ggt        960
Tyr Asp Arg Phe Ala Pro Val Lys Ile Leu Lys Leu Asp Tyr Asp Gly
305                 310                 315                 320 ttg aat tat gag aaa cat atc gat gct gaa tac gag cca tca aat cat        1008
Leu Asn Tyr Glu Lys His Ile Asp Ala Glu Tyr Glu Pro Ser Asn His
                325                 330                 335 tac aaa tac ttt acc gat ggt aaa tcg aag aga agt ggc aaa ggt tat        1056
Tyr Lys Tyr Phe Thr Asp Gly Lys Ser Lys Arg Ser Gly Lys Gly Tyr
            340                 345                 350 tcg atc aaa atc gat gga aaa cca aag aaa gca ttg aaa gtt gat gtc        1104
Ser Ile Lys Ile Asp Gly Lys Pro Lys Lys Ala Leu Lys Val Asp Val
        355                 360                 365 gat atg ccg gat ttt aaa ttc aat gtg aac aaa ccg gaa gat agt aac        1152
Asp Met Pro Asp Phe Lys Phe Asn Val Asn Lys Pro Glu Asp Ser Asn
370                 375                 380 aaa gct caa ttt agt tat aca ttc aat gat tat acc gaa acg gaa gag        1200
Lys Ala Gln Phe Ser Tyr Thr Phe Asn Asp Tyr Thr Glu Thr Glu Glu
385                 390                 395                 400 tat gaa ttc gat cca cat cgt gca tat atc ttg aat tgg gcc aga gct        1248
Tyr Glu Phe Asp Pro His Arg Ala Tyr Ile Leu Asn Trp Ala Arg Ala
                405                 410                 415 atc aga caa tat ttg cag aca ttc att gtt gag tag                        1284
Ile Arg Gln Tyr Leu Gln Thr Phe Ile Val Glu
                420                 425
```

<210> SEQ ID NO 2
<211> LENGTH: 427
<212> TYPE: PRT
<213> ORGANISM: Sarcoptes scabiei

<400> SEQUENCE: 2

```
Glu Ala Glu Val Thr Phe Ser Asp Ser Glu Asp Lys Lys Asn Tyr Phe
1               5                   10                  15

Val Glu Leu Lys Lys Asp Lys Asp Leu Tyr Ser Met Lys Ser Asn Val
            20                  25                  30

Lys Arg Asn Asn Glu Ile Phe Tyr Glu Asn Asn Met Asp Leu Glu Lys
        35                  40                  45

Asn Gly Lys Met Asn Trp Tyr Tyr Lys Arg Asn Asp Arg Thr Trp Asn
    50                  55                  60

Met Asp Leu Asp Asn Ala Phe Asn Pro Arg Asp Gly Thr Met Lys Leu
65                  70                  75                  80

Gln Val Lys Asp Arg Ile Tyr Asp Ile Lys Leu Lys Arg Glu Arg Phe
                85                  90                  95

Arg Tyr Gly Asp Leu His Ile Glu Gly Asn Glu Asn Pro Leu Ile Lys
            100                 105                 110

Lys Gly Asp Leu His Met Ser Leu Val Asp Pro Leu Thr Leu Asn Val
        115                 120                 125

Leu Thr Lys Asn Asp Gly Ile Val Asp Met Thr Leu Asp Leu Val Ser
    130                 135                 140
```

-continued

```
Pro Asn Thr Lys Lys Ala Ala Leu Lys Ile Asn Ser Lys Lys Tyr Asp
145                 150                 155                 160

Leu Asp His Asp Gly Glu Ile Thr Val Ser Ile Phe Asn Pro Arg Met
                165                 170                 175

Thr Trp Lys His His Thr Arg Lys Gly Asp Met Glu Leu Asn Ile Asp
            180                 185                 190

Ala Asp Ile Thr Arg Lys Gly Ser Leu Ile Thr Tyr Ser Arg Lys Glu
        195                 200                 205

Pro Asp Asp Ser Thr Lys Val Arg Tyr Ser Arg Gln Gly Asn Gln Val
210                 215                 220

Ser Met Glu Val Asp Ser Lys Leu Ile Glu Gly His Ala Asn Gly Thr
225                 230                 235                 240

Leu Thr Asp Gly Lys Ile His Val Lys Gly Arg Glu Ser Asp Phe Glu
                245                 250                 255

Ile Glu Ser Thr Tyr Lys Val Glu Asp Gly Lys Leu Met Ile Glu Pro
            260                 265                 270

Thr Lys Thr Gln Asn Gly Lys Leu Glu Gly Leu Leu Ser Arg Lys Val
        275                 280                 285

Pro Ser His Leu Val Leu Glu Thr Pro Arg Val Lys Met Asn Met Lys
290                 295                 300

Tyr Asp Arg Phe Ala Pro Val Lys Ile Leu Lys Leu Asp Tyr Asp Gly
305                 310                 315                 320

Leu Asn Tyr Glu Lys His Ile Asp Ala Glu Tyr Glu Pro Ser Asn His
                325                 330                 335

Tyr Lys Tyr Phe Thr Asp Gly Lys Ser Lys Arg Ser Gly Lys Gly Tyr
            340                 345                 350

Ser Ile Lys Ile Asp Gly Lys Pro Lys Ala Leu Lys Val Asp Val
        355                 360                 365

Asp Met Pro Asp Phe Lys Phe Asn Val Asn Lys Pro Glu Asp Ser Asn
370                 375                 380

Lys Ala Gln Phe Ser Tyr Thr Phe Asn Asp Tyr Thr Glu Thr Glu Glu
385                 390                 395                 400

Tyr Glu Phe Asp Pro His Arg Ala Tyr Ile Leu Asn Trp Ala Arg Ala
                405                 410                 415

Ile Arg Gln Tyr Leu Gln Thr Phe Ile Val Glu
            420                 425
```

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Ser Arg Cys Asp Leu Gln His His His His His
  1               5                  10
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
cactatcgga gaacgtaact tcgg                                           24

-continued

```
<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
cctggcattc tacttgagat gta                                           23

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
cgctctagac tcaacaatga atgtctgcaa                                    30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
cgggatccga atatttcgtc tcgaaaccg                                     29
```

MITE PROTEIN

TECHNICAL FIELD

The present invention relates to a novel recombinant protein useful in the diagnosis of mite infections in mammals, such as dogs. The invention also relates to a nucleic acid encoding the protein according to the invention as well as to various advantageous uses thereof.

BACKGROUND

Scabies or *sarcoptic* mange, which is caused by infection with the parasitic mite *Sarcoptes scabiei*, is a widespread, highly contagious disease. The parasite has been found in well over 40 different mammals, including man. During the infection, female mites burrow in the skin to feed and their activities cause an intense irritation that leads to itching and scratching, which may aggravate the condition. Sensitization of the host to the mites and their products probably plays an important role in the pathogenesis of the disease. In its extreme form, scabies can develop into a severe hyperkeratotic form, where several thousands of mites can be found in the lesions. This form of crusted scabbies is also frequently observed among immune compromised individuals, i.e. HIV patients.

The standard method for diagnosing scabies include microscopic detection of the mites and their eggs and feces in skin scrapings. This method is relatively time-consuming and, in many cases, the results of microscopic examination can be negative owing to the low number of parasites present in each sample. The use of enzyme-linked immunosorbent assays (ELISA) for the detection of antibodies to *S. scabiei* has been reported for several different animals including humans (Bornstein & Zakrisson (1993) *Vet. Dermatol.* 4:107; Arlian et al. (1994) *Exp. Parasitol.* 78:37; Normaznah et al. (1996) *Southeast Asian J. Trop. Med. Public Health* 27:53; and Hollanders et al. (1997) *Vet. Parasitol.* 69:117). The ELISA technology offers several distinct advantages compared to skin scrapings: A relative ease of sampling, the potential to screen large numbers of samples and the possibility to standardize reagents and methods. The only major drawback is the limited amount of antigenic material available due to the lack of an in vitro propagation system for *S. scabiei*.

Arlian and colleagues (J. Med. Entomol. (1988) 25:52) have developed an in vivo propagation system after establishing *S. scabiei* var. *canis* on rabbits. However, the parasite burden is still relatively low and the method cannot be applied for the production of antigens for large scale screening projects. Mites from naturally infected red foxes have been successfully isolated in large numbers and used in ELISAs both for dogs and pigs. The difficulties involved in using wild foxes as a source for antigen supply are however evident.

This lack of material has not only limited large scale screening efforts and control programs among farm animals, but it has also limited the possibilities to study other aspects of scabies, for instance pathogenesis.

EP 0 473 111 provides a recombinant mite allergen which is effective as a therapeutic agent and diagnostic reagent for mite allergic diseases. However, the mite allergen of this reference are derived from a house dust mite, more specifically from *Dermatophagoides farinae*. Thus, firstly, the said house dust mite is found free-living in a house-hold environment and does not live as a parasite on a host. Thus, disease thereof is not the result of an infection but the inhalation of mites or mite body fragments or faeces. The inhalation of house dust mites may cause allergic reactions in susceptible individuals resulting in respiratory distress, such as asthma and rhinitis. Accordingly, EP 0 473 111 relates to molecules useful in the diagnosis and prevention of such conditions.

SUMMARY OF THE INVENTION

According to the present invention, the problems defined above are solved by providing a novel major mite antigen, which has now been isolated and sequenced for the first time. Thus, the invention relates an isolated antigenic protein as well as to the nucleic acid said novel protein, as defined in the appended claims. Further, the invention also relates to various advantageous uses of the novel protein and functional fragments thereof, e.g. in immunological testing, such as in ELISA methods.

DEFINITIONS

Figure 1:
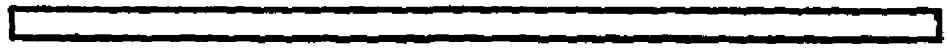
FIG. 1 shows the extent of the recombinant protein according to the invention in relation to the native protein.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point Tm for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupies at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in a ELISA), biotin, dioxigenin, or haptens and proteins for which antisera or monoclonal antibodies are available.

As used herein a "nucleic acid probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, C, U or T) or modified bases (7-deazaguanosine, inosine, etc.) In addition, the bases in a probe may be joined by a linkage other than a phosphodiester bond, so long as it does not interfere with hybridization.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "target nucleic acid" refers to a nucleic acid (often derived from a biological sample), to which a nucleic acid probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the ovarall sequence (e.g., gene or mRNA) whose expression level it is desired to detect. The difference in usage will be apparent from context.

"Subsequence" refers to a sequence of nucleic acids or amino acids that comprise a part of a longer sequence of nucleic acids or amino acids (e.g., polypeptide), respectively.

"Combinatorial library" means a library of molecules containing a large number, typically between $10^3$ and $10^6$, of different-sequence oligomers, typically characterized in having different sequences or subunits, or a combination of different sequences of side chains and linkages, or different-substituent compounds in a small-compound library.

"Different-sequence oligomer compounds" are oligomers, such as oligonucleotides, oligonucleotide analogs, oligopeptides, oligopeptide analogs, oligosaccharides, or lipopeptides with different permutations of lipid and/or sequences in the peptide moieties, glycopeptides with different sequence permutations in the saccharide and/or peptide moieties, non-biological oligomers with different-sequence permutations, or different-substituent compounds in a small-compound library.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all. Further, the expression "recombinant" also relates to a cell, wherein further regulatory elements have been included in order to initiate or enhance expression of an otherwise silent endogenous gene, or wherein a manipulation of the regulatory elements have been performed for the same purpose. (For an example of such a gene activation technique, see e.g. *Genetic Engineering News*, Apr. 15, 1994.)

The term "identical" in the context of two nucleic acid or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Natl. Acad. Sci.* USA 85: 2444, by computerized implementations of these algorithms (GAP, BESTFIT, FASTA, and TFASTA in the Wisconsin Genetics Software Package, Genetics Computer Group, 575 Science Dr., Madison, Wis.) or by inspection.

An additional algorithm that is suitable for determining sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). (See Henikoff and Henikoff (1992) *Proc. Natl. Acad. Sci. USA* 89: 10915–10919; and Karlin and Altschul (1993) *Proc. Natl. Acad. Sci. USA* 90: 5873–5787; for further information in this context.)

The term "substantial identity" or "substantial similarity" in the context of a polypeptide indicates that a polypeptides comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid. Another indication that two nucleic acid sequences are substantially identical is that the two molecules hybridize to each other under stringent conditions.

"Bind(s) substantially" refers to complementary hybridization between a probe nucleic acid and a target nucleic acid and embraces minor mismatches that can be accomodated by reducing the stringency of the hybridization media to achieve the desired detection of the target polynucleotide sequence.

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu alpha, delta, or epsilon, which in turn define the immunoglobulin classes, IgG, IgM, IgA, IgD and IgE, respectively. (In this context, see *Fundamental Immunology*, Third Edition, W. E. Paul, ed., Raven Press, N.Y. 1993).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantify the analyte. The terms "isolated" "purified" or "biologically pure" refer to material which is substantially or essentially free from components which normally accompany it as found in its native state.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbour Publications, New York, for a description of immunoassay formats and conditions that can be used to determine specific immunoreactivity.

A "conservative substitution", when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. See e.g., Creighton (1984) *Protein*, W.H. Freeman and Company. In addition, individual substitutions, deletions or additions which alter, add or delete a single amino acid or a small percentage of amino acids in an encoded sequence are also "conservatively modified variations".

A "gene product", as used herein, refers to a nucleic acid whose presence, absence, quantity, or nucleic acid sequence is indicative of a presence, absence, quantity, or nucleic acid composition of the gene. Gene products thus include, but are not limited to, an mRNA transcript, a cDNA reverse transcribed from an mRNA, and RNA transcribed from that cDNA, a DNA amplified from the cDNA, an RNA transcribed from the amplified DNA or subsequences of any of these nucleic acids. Polypeptides expressed by the gene or subsequences thereof are also gene products. The particular type of gene product will be evident from the context of the usage of the term.

DETAILED DESCRIPTION OF THE INVENTION

In a first aspect, the present invention relates to an isolated mite-derived protein, which is an antigen derived from the mite *Sarcoptes scabiei*. More specifically, the protein according to the invention is comprised of parts or all of the sequence disclosed in SEQ ID NO. 2. More specifically, the invention relates to a protein comprised of at least about 83 amino acids of said sequence, preferably the ones described in SEQ ID NO. 3, an analogue or a functional fragment thereof. In a specific embodiment, the protein according to the invention is comprised of at least about 100 amino acids, preferably at least about 200, such as at least about 400 amino acids of the sequence disclosed in SEQ ID NO. 2. In a specific embodiment, the protein according to the invention comprises about 400 of the last amino acids of SEQ ID NO 2, and most preferably, the sequence from about amino acid no 344 to amino acid no 770 of said sequence, which protein has been denoted Major *Sarcoptes* Antigen 1 (MSA1) of the present inventors. In another particular embodiment, the amino acid sequence of the present protein comprises a larger part of said sequence, such as at least about 400, preferably at least about 500, e.g. at least about 600, and most preferably at least about 700, such as about 770 amino acids of said sequence, in which case it is substantially identical with the sequence disclosed in SEQ ID NO. 2. In this context, it is to be understood that all derivatives, analogues and functional fragments and functional subsequences thereof of the present proteins also fall within the scope of the invention as defined by the claims.

Thus, the above mentioned EP 0 473 111 relates to the isolation of an organism, house dust mite, which is naturally present in different surroundings than *Sarcoptes scabiei*, which is a parasite in the skin of animals, such as wild foxes, swine etc., and man. As a consequence, the pharmaceutical and diagnostic applications enabled by the EP 0 473 111 antigen are suited for different conditions and other subjects than the antigen according to the present invention, which mainly relates to the treatment and/or diagnosis of farm animals, such as swine, or dogs. Accordingly, even though there exist a certain similarity between the protein derived from the house dust mites according to EP 0 473 111 and the *Sarcoptes scabiei* protein isolated and sequenced according to the present invention, the differences in environment and conditions to be prevented and/or diagnosed are of such importance that 0 473 111 must be regarded as relating to a different field from the present invention.

In an especially advantageous embodiment, the protein according to the invention is a recombinant protein, which in addition to a functional part or all of the sequence disclosed in SEQ ID NO. 2 also comprises a tag, such as a conventional further amino acid sequence, which confers properties that facilitates purification, downstream analysis, such as Western blot, reversible immobilization, immunoprecipitation, immunofluorescence analysis etc. Said tag may e.g. be the peptide His6. In a particular embodiment, the present invention is a fusion protein, wherein the present protein or a functional subsequence thereof is fused with another protein, such as β-galactosidase, glutathione-S-transferase, protein A etc. In the context of fusion proteins, see e.g. Smith and Johnson (1988) *Gene* 67:31; Hopp et al. (1988) *Biotechnology* 6:1204; La Vallie et al. (1993) *Biotechnology* 11: 187.

In a further embodiment, the present protein, or a functional subsequence thereof, is used to produce peptidomimetics, i.e. molecules that mimics the biological activity of the peptide but no longer are completely peptidic in nature. Thus, peptidomimetics according to the invention are produced in order to provide molecules that are more advantageous than the peptides per se as regards e.g. size, bioavalability, duration of action, stability, storage, immunoreactivity etc. In this context, see e.g. Dean (1994), *BioEssays,* 683–687, Cohen and Shatzmiller (1993), *J. Mol. Graph.,* 11:166–173.

Further, the antigen according to the invention may be used in various other methods for design and/or identification of novel compounds, such as in combinatorial libraries. Such methods enable a modem drug laboratory to produce and screen millions of new chemical and/or biological compounds in a few weeks for a variety of uses. Of the large number of compounds produced, only the ones showing interesting biological activity are analyzed for further testing and experimentation. Methods for combinatorial libraries, see e.g. U.S. Pat. Nos. 5,753,187 and 5,763,263, are well known to those of skill in this field and are easily arranged based on the present application. A further aspect of the present invention is the use of the antigen according to the invention in methods of high-throughput screening for the identification of a novel compound. Such methods are amenable to automated, cost-effective high throughput screening and have immediate application in a broad range of programs for development of diagnostic and/or pharmaceutically active compounds. Further, the present invention also encompasses any compound obtainable by, that is, reached through, the use of any one of the herein disclosed methods.

Thus, more specifically, the present invention also relates to a method of screening for protein or peptide analogues that mimic at least a part of the structure of the protein according to the invention, which comprises the steps of
(a) producing a multiplicity of analogue structures and
(b) selecting an analogue structure, wherein the three-dimensional configuration and spatial arrangement of one or more biologically active regions, preferably anti-genic regions, remain substantially preserved.

In a specific embodiment, analogues mimicking a protein having the amino acid sequence as disclosed in SEQ ID NO 3 are screened for. Further, the invention also encompasses an analogue identified as disclosed above. Analogues identified by the present method are advantageously used for the same purposes as the proteins according to the invention, said various uses being disclosed elsewhere in the present disclosure.

The present proteins, functional subsequences thereof etc. may be synthesized using standard chemical peptide synthesis techniques. Where the desired subsequences are relatively short (e.g., when a particular antigenic determinant is desired), the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis, Part A.*, Merrifield, et al. *J. Am. Chem. Soc.,* 85: 2149–2156 (1963), and Stewart et al., *Solid Phase Peptide Synthesis, 2nd ed*. Pierce Chem. Co., Rockford, Ill. (1984).

In an alternative embodiment, the present proteins or subsequences thereof, are synthesized using recombinant DNA methodology. Generally this involves creating a DNA sequence that encodes the fusion protein, placing the DNA in an expression casette under the control of a particular promoter, expressing the protein in a host, isolating the expressed protein and, if required, renaturing the protein.

DNA encoding the present proteins, or subsequences thereof, may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth Enzymol.* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences. Similarly, subsequences may be cloned and the appropriate subsequences cleaved using appropriate restriction enzymes. The fragments may then be ligated to produce the desired DNA sequence.

In one embodiment, proteins of this invention may be cloned using DNA amplification methods such as polymerase chain reaction (PCR). Thus, for example, the nucleic acid sequence or subsequence is PCR amplified, using a sense primer containing one restriction site, e.g., XhoI, and an antisense primer containing another restriction site, e.g., BamHI. This will produce a nucleic acid encoding the desired sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the information provided in the appended sequence listing. Appropriate restriction sites can also be added to the nucleic acid encoding the protein or protein subsequence by site-directed mutagenesis. The plasmid containing the sequence or subsequence is cleaved with the appropriate restriction endonuclease and then ligated into the vector encoding the second molecule according to standard methods.

Accordingly, in a second aspect, the present invention relates to an isolated nucleic acid encoding the protein according to the present invention. More specifically, the present invention relates to a nucleic acid comprising parts or all of the base sequence disclosed in SEQ ID NO. 1, such as about 200–2000, e.g. at least about 400, such as at least about 1000, and preferably at least about 2300 bases thereof. In a specific embodiment of this aspect, the nucleic acid according to the invention comprises about the second half of the sequence of SEQ ID NO 1, preferably at least about 1200, e.g. 1284, and most preferably, the 1284 bases that encodes the protein denoted MSA1 which is discussed above. In another embodiment of this aspect of the invention, the nucleic acid is substantially identical with the sequence of SEQ ID NO 1. In a particularly advantageous embodiment, the present nucleic acid encodes a protein as disclosed by SEQ ID NO 3. In the present context, it is to be understood that the invention also encompasses any one of the above defined sequences which is a degenerate or variant thereof.

Further, this aspect of the invention also covers any nucleic acid, which hybridizes specifically under stringent conditions to a nucleic acid as disclosed above as well as any gene product obtained thereby. Such a hybridizing nucleic acid may e.g. be DNA, a genomic DNA sequence comprising introns as well as exons, RNA, such as mRNA etc.

The preparation of the present nucleic acids has already been described above. Thus, more specifically, the sequences are cloned, or amplified by in vitro methods, such as the polymerase chain reaction (PCR), the ligase chain reaction (LCR), the transcription-based amplification system (TAS), the self-sustained sequence replication system (SSR). A wide variety of cloning and in vitro amplification methodologies are known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current protocols in Molecular Biology*, F. M. Ausubel et al., Current Protocols, a joint venture between Greene Publishing Associates, Inc. And John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. Eds) Academic Press Inc. San Diego, Calif. (1990) (Innis); Arnheim & Levinson (Oct. 1, 1990) *C&EN* 36–47; *The Journal of NIH Research* (1991) 3: 81–94 (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89: 117.

In one preferred embodiment, the nucleic acids according to the invention are isolated by routine cloning methods. The DNA sequence provided in SEQ ID NO 1, or a subsequence thereof, can be used to provide probes that specifically hybridize to the encoding gene, in a genomic DNA sample, e.g. in a Southern blot, or to the mRNA, in a total RNA sample (e.g., in a Northern blot). Once the target nucleic acid has been identified (e.g., in a Northern or Southern blot), it is isolated according to standard methods known to those of skill in the art (see, e.g., Sambrook et al. (1989) *Molecular Cloning: A Laboratory Manual, 2nd Ed.* Vols. 1–3, Cold Spring Harbor Laboratory; Berger and Kimmel (1987) *Methods in enzymology, Vol.* 152: *Guide to Molecular Cloning Techniques*, San Diego: Academic press, Inc.; or Ausubel et al. (1987) *Current Protocols in Molecular Biology*, Greene Publishing and Wiley-Interscience, New York).

The nucleic acids according to the invention may be used in assays, such as in hybridization assays, as probes, in which case they are preferably labeled, in the production of proteins according to the invention etc., as is evident from other sections of the present specification.

A further aspect of the invention is an expression vector, such as a plasmid or a virus, such as a phage, which comprises a nucleic acid as describe above. Such vectors are e.g. useful for expressing the proteins according to the invention to provide immunogens for antibody production. Thus, vectors encoding the proteins are also useful for transforming cells in vitro or in vivo to express the present protein or a functional subsequence thereof. In addition to the present encoding sequence, the vectors according to the invention also comprise suitable promoters, enhancers and further regulatory elements operably linked thereto (Queen et al. (1986) *Immunol. Rev.* 89:49). The vector may be a plasmid, virus, etc. Further, the vector may be an oligonucleotide, in which case the coding sequence may be accompanied by the required tagging sequences for use in methods such as homologous recombination, as described in the literature.

Thus, an additional aspect of the present invention is a recombinant cell comprising a vector according to the invention. The culture of cells, including cell lines and cultured cells from tissue or blood samples, is well known in the art. (See e.g. Freshney, *Culture of Animal Cells, A Manual of Basic Technique*, 3$^{rd}$ ed., Wiley-Liss, New York, N.Y. (1994).) Cells expressing the present nucleic acid may be used to monitor expression levels of the protein according to the invention in a wide variety of contexts. The cells according to the invention may be prokaryotic, such as bacteria, e.g. *E. coli*, eukaryotic, such as yeast, mammalian, such as canine, porcine or human, a protozoan etc.

In an additional aspect, the invention relates to a method for producing a protein according to the invention, or a functional subsequence thereof, which method comprises the steps of (a) providing a DNA encoding the desired protein or polypeptide;

(b) introducing said DNA in a suitable expression vector or expression cassette;

(c) transfer of said vector or cassette into a suitable cell;

(d) culturing said cell to obtain the desired product; and optionally (e) purification of the protein or polypeptide.

The transfer of the vector may be performed by well-known methods, depending on the type of cellular host, such as calcium chloride transfection, which is commonly used with prokaryotic cells, or calcium phosphate treatment, electroporation, lipofection, microinjection etc. Once expressed, the products may be purified according to standard procedures in the art, such as HPLC purification, fraction column chromatography, gel electrophoresis and the like (see e.g. Scopes, *Protein Purification*, Springer-Verlag, N.Y., 1982).

In a further aspect, the present invention relates to an antibody raised against a protein according to the invention, or a functional part thereof. The antibody according to the invention will preferably comprise at least about 10, more preferably at least 20, 40 or 50 and most preferably at least 100 or 200, or even 400 amino acids. In a specific embodiment, the antibody binds to a protein comprised of essentially all of the sequence disclosed in SEQ ID NO 2.

More specifically, the present invention relates to antibodies including individual, allelic, strain, or species variants, and fragments thereof, both in their naturally occurring (full-length) forms and in recombinant forms. Additionally, antibodies are raised to these polypeptides in either their native configurations or in non-native configurations. Anti-idiotypic and chimeric or bispecific antibodies can also be generated.

In order to produce the antibodies specifically reactive with polypeptides according to the invention, a number of immunogens are used. Recombinant or synthetic polypeptides of 8–15, preferably 10, amino acids in length, or greater, selected from amino acid sub-sequences of SEQ ID NO 2 are the preferred polypeptide immunogen (antigen) for the production of monoclonal or polyclonal antibodies. In one class of preferred embodiments, an immunogenic peptide conjugate is also included as an immunogen. Naturally occuring polyptides are also used, either in pure or impure form.

Recombinant polypeptides are expressed in eukaryotic or prokaryotic cells (as described above) and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypetide.

Methods of producing polyclonal antibodies are known to those of skill in the art, see, e.g., Coligan (1991) *Current Protocols in Immunology* Wiley/Greene, N.Y.; and Harlow and Lane (1989) *Antibodies: A Laboratory Manual* Cold Spring Harbor Press, NY).

Monoclonal antibodies are prepared from cells secreting the desired antibody. These antibodies are screened for binding to normal or modified polypeptides, or screened for agonistic or antagonistic activity, e.g., activity mediated through a suppressor of fused protein. Specific monoclonal and polyclonal antibodies will usually bind with a $K_D$ of at least about 0.1 mM, more usually at least about 50 µM, and most preferably at least about 1 µM or better.

In some instances, it is desirable to prepare monoclonal antibodies from various mammalian hosts, such as dogs, swine, rodents, primates, humans, etc. Description of techniques for preparing such monoclonal antibodies are found in, e.g. Stites et al. (eds) *Basic and Clinical Immunology* (4th ed.) Lange Medical Publications, Los Altos, Calif., and references cited therin; Harlow and Lane, supra; Goding (1986) *Monoclonal Antiboides: Principles and Practice* (2d ed.) Academic Press, New York, N.Y.; and Kohler and Milstein (1975) *Nature* 256: 495–497.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

In a further aspect, the present invention relates to a protein as defined above, or a functional subsequence thereof, for use in a pharmaceutical preparation, preferably as a vaccine. Thus, the invention also relates to a vaccine preparation comprising a protein as defined above and a pharmaceutically acceptable carrier, such as an aqueous carrier. A variety of aqueous carriers may be used, e.g. buffered saline. The solution is sterile and generally free of any undesirable matter. It may contain further auxiliary substances as required to approximate physiological conditions, such as pH adjusting agents and buffers, toxicity adjusting agents, e.g. sodium acetate, sodium chloride, potassium chloride, sodium lactate etc. It may be prepared for injection or any other suitable route of administration, such as oral administration. For a brief review of drug delivery, see Langer, Science 249:527–1533 (1990).

More specifically, the vaccine preparation according to the invention is capable of provoking an immune response in a subject, such as an animal or human, and thereby preventing said subject from being infected with *Sarcoptes scabiei*, whereby *sarcoptes* mange or scabies is avoided. Thus, the vaccine composition according to the invention may advantageously be used to immunize animals, e.g. dogs or swine. As one example, dogs may be infected with scabies or sarcoptic mange from wild animals in the surroundings, such as red fox. Swine is another species that may be infected with scabies or sarcoptic mange. For example, when piglets are transported to novel locations during the breeding thereof, they may be contacted with other stock and the infection may then be spread. The vaccine composition may be a killed or inactivated, attenuated, recombinant or subunit vaccine, as appropriate, depending on the prevailing conditions.

Thus, the invention also relates to a method of preventing mite diseases, preferably conditions caused by mites, such as *Sarcoptes scabiei*, in a subject, such as a human, or animal, such as a canine or porcine, subject, which method comprises the administration of a pharmaceutical preparation according to the invention to said subject in an effective dose. In a specific embodiment, said disease is *sarcoptes* mange or scabies.

The invention also relates to any medicinal use of the proteins and polypeptides according to the invention. As regards the pharmaceutical uses of the present polypeptides, it is to be understood, that in many cases, it may be more advantageous to use the peptidomimetics according to the invention than the original polypeptides. Such uses are also within the scope of the invention.

In one furter aspect, the invention relates to various assays, wherein an antibody according to the invention is used to determine the presence and/or quantity of the polypeptide. The methods include analytical biochemical methods, such as electrophoresis, high performance liquid chromatography (HPLC), thin layer chromatography (TLC), hyperdiffusion chromatography and the like as well as various immunological methods, such as fluid or gel precipitating reactions, immunodiffusion, immunoelectrophoresis, radioimmunoassay (RIA), enzyme-linked immunosorbent assays (ELISAs), immunofluorescence assays etc. As used herein, an immunoassay is an assay wherein an antibody is used to specifically bind to the analyte. In the present context, such an assay format as disclosed in EP 291 194 (Unilever) is advantageously used, or variants of said format specifically adapted to the present purpose. For a review of general immunoassays, see *Methods in Cell Biology*, Vol. 37: *Antibodies in Cell Biology*, Asai, ed., Academic Press, Inc., New York (1993); and *Basic and Clinical Immunology*, 7th ed., Stites & Terr, eds., (1991).

Competitive assay formats are preferred in the present context, wherein the amount of analyte, preferably an unknown quantity of antibodies in a subject, in a sample is measured indirectly by measuring the amount of added analyte, displaced from a capture agent by the analyte present in the sample. Most preferred are the enzyme-linked immunosorbent assay (ELISA) methods, in which an antibody typically is bound to an enzyme, such as peroxidase or phosphatase, which can produce colored reaction products from an appropriate buffer. Thus, it utilizes a tagged antigen molecule of known quantity to determine an unlabelled antigen of unknown quantity. Preferably, the protein according to the invention, or a suitable functional fragment thereof, is used coupled to a conventional tag, such as His6. This assay is e.g. useful to diagnose *Sarcoptes scabiei* infection in dogs.

Thus, in an ELISA format according to the invention, antibodies against the present polypeptide are detected and/or quantified, preferably in a biological sample. The sample may be any sample of biological tissue or fluid, such as blood. The sample is pretreated as necessary by dilution in a suitable buffer solution or concentrated, if desired. Any number of standard aqueous buffer solutions may be used, such as Tris or the like, at physiological pH. Samples are incubated with an excess of the protein according to the invention as antigen. After rinsing to remove any unbound antibody, the amount of bound antibody is quantitated by adding a solution of enzyme-conjugated antibody that binds to constant domains of antibodies in the sample. Excess conjugated antibody is rinsed away and the activity of the bound enzyme is determined by adding the substrate to the reaction and measuring the formation of products. As the products of the reactions used in ELISA procedures are colored, the amount of product formed can readily be be determined by the intensity of the colour that has developped using a spectrophotometer. The activity of the bound enzyme is proportional to the amount of antigen-binding antibody in the sample; therefore, the original concentration of such antibodies can be estimated from a series of control assays employing known concentrations of specific antibodies.

More specifically, if a protein as defined by SEQ ID NO. 2 coupled to His6 is used, it has been shown by the present inventor that an antigen concentration of about 30–60 ng/ml is advantageous. It is essential that protein contamination is prevented in order to avoid an enhanced background. Further, the coating ratio should be adapted as appropriate in order to improve the background. Presumably, the aftercoating is not critical.

Consequently, the invention also relates to a kit for the diagnosis of a subject infected with a mite, preferably *Sarcoptes scabiei*. More specifically, the kit according to the invention is adapted for performing the above disclosed ELISA method. Such a kit will include one or more reagents for determining the presence or absence of antibodies in the subject raised against the polypeptides according to the invention. The antigen may be free or immobilized on a solid support, such as a test tube, a microtiter plate, a dipstick or the like. The kit may also comprise instructions for the use thereof. The kit may also contain means for the detection of labels, positive and negative controls, washing solutions etc. More specifically, a kit according to the present invention may advantageously comprise a conjugate, positive and negative control samples, a serum dilution buffer, a substrate, suitable washing solutions as well as an appropriate conjugate dilution buffer.

DETAILED DESCRIPTION OF THE DRAWINGS

FIG. 1 shows the extent of the recombinant protein according to the invention in relation to the native protein.

Figure 2:
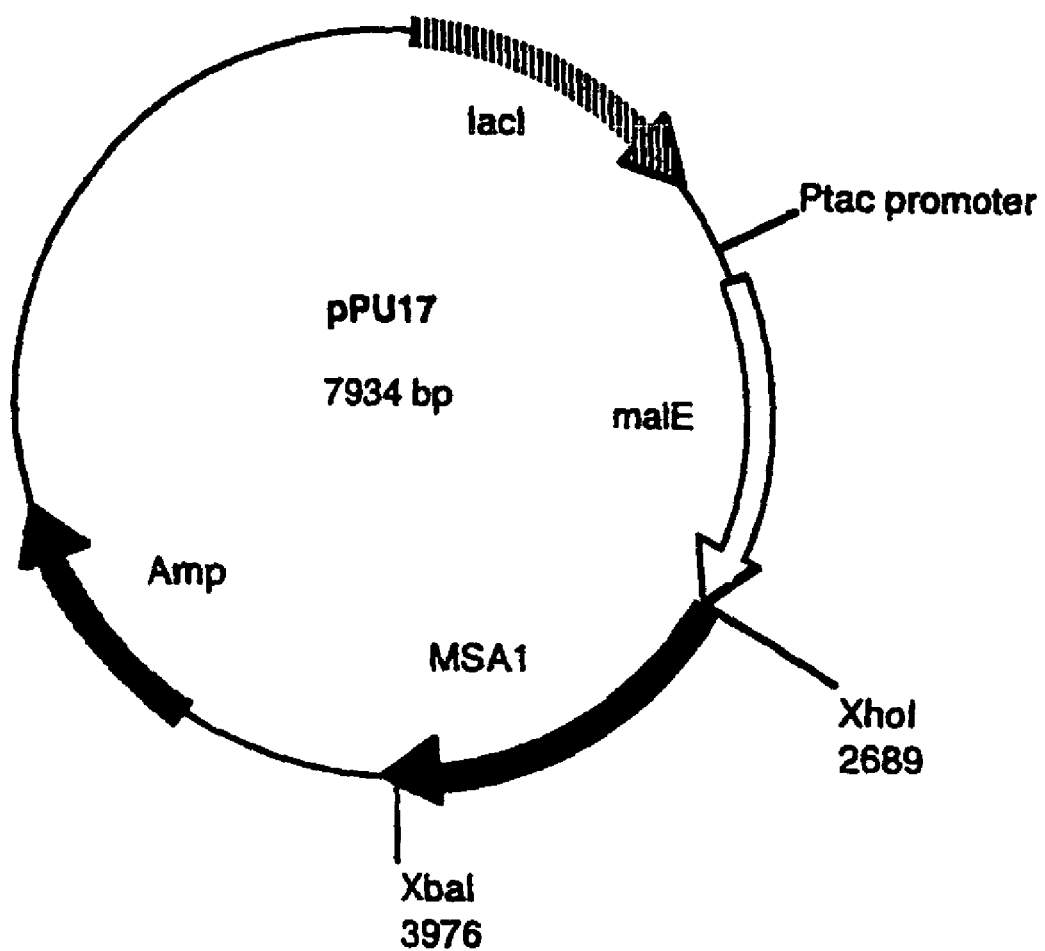
FIG. 2 illustrates the recombinant plasmid pPU17 used for the expression of the mite protein according to the invention.

FIG. 2 illustrates the recombinant plasmid pPU17 used for the expression of the mite protein MSA1 according to the invention. Amp is the ampicillin resistance gene, lacI is the lac repressor gene, and male is the maltose binding protein in fusion with the present MSA1.

Figure 3:
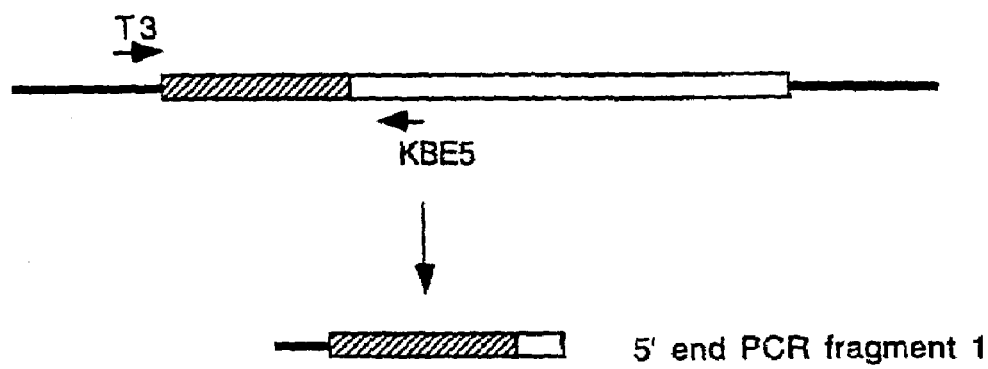
FIG. 3 is an overview of the cloning strategy of the 5' end of MSA.
Figure 3:
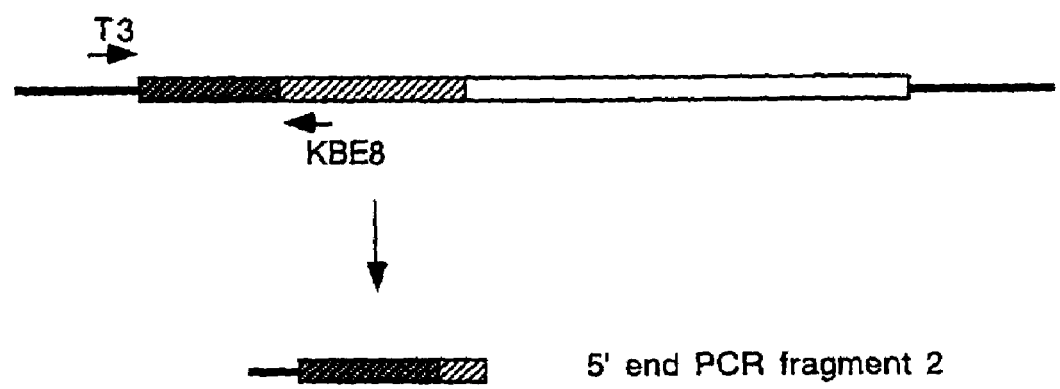
Figure 3:
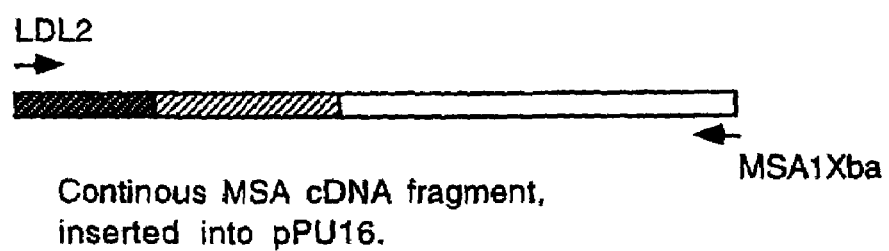

FIG. 3 is an overview of the cloning strategy of the 5' end of MSA.

Figure 4:
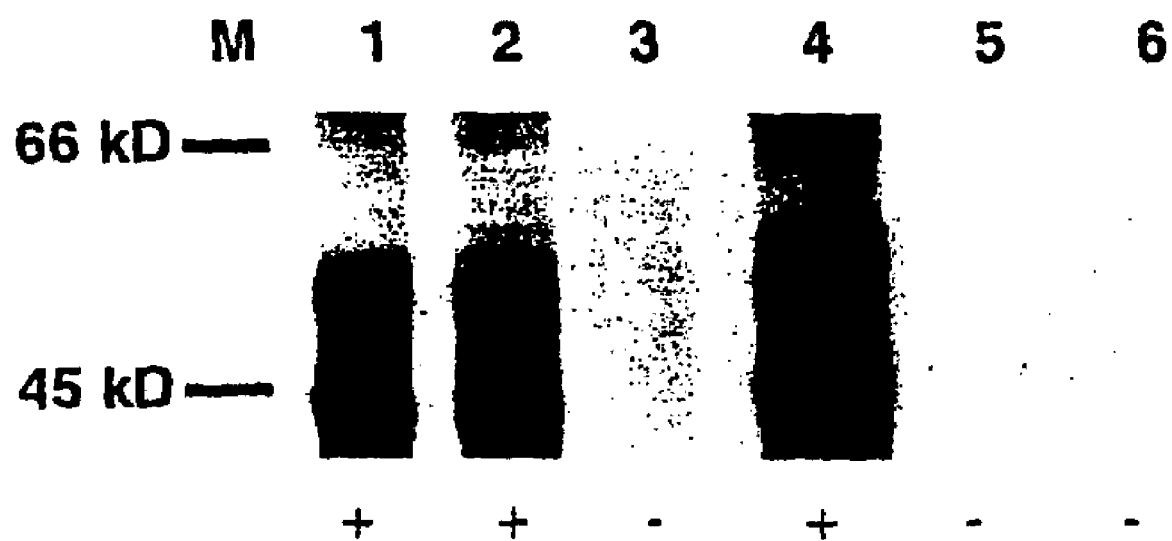
FIG. 4 shows the results of Western blot analysis of the mite recombinant protein according to the invention.

FIG. 4 shows the results of Western blot analysis of the mite recombinant protein MSA1 according to the invention.

The protein was expressed in *E. coli*, purified and separated by SDS-PAGE before transfer to nitrocellulose. Lanes 1, 2 and 4 show the results after analysis with positive dog sera, and lanes 3, 5 and 6 shows the results after analysis with negative dog sera. Lane M is the molecular weight markers.

Experimental

Material and Methods

Collection of Parasites

Living mites of both sexes and different developmental stages of *S. scabiei* were isolated from the skin of wild red foxes as described in Bornstein & Zakrisson (1993) *Vet. Dermatol.* 4:107. Briefly, pieces of skin with the fur cut down to about 10 mm were left in Petri dishes at room temperature under an electric light. Mites that migrated onto the underside of the lid were collected and stored at −70° C. until further use.

Immunosera

*S. scabiei* proteins of a size of above 90 kD were size-selected on 10% gels by sodium dodecyl sulfate-polyacrylamide gel electrophoresis (SDS-PAGE) and electroeluted as previously described, see Jacobs & Clad (1986) Anal. Biochem. 154:583. New Zeeland White rabbits were immunized with the selected proteins and Freund's complete adjuvant.

RNA Preparation and Construction of cDNA Library

A total of 160 mg of mites was washed with PBS and then homogenized in a glass grinder at 4° C. Total RNA was extracted with an RNAgents® kit from Promega and mRNA was isolated by oligo(dT) cellulose chromatography (Pharmacia Biotech). Double-stranded cDNA was synthesized from about 5 μg *S. scabiei* mRNA (ZAP-cDNA, Stratagene), portions ligated into UNI-ZAP XR vector (Stratagene) and packaged into λ-phage (Gigapack Gold II, Stratagene).

Cloning and Sequencing of MSA1

The amplified library was screened with sera from the rabbits previously immunized with gel purified antigens. Immuno reactive plaques were cloned and the phages eluted. From a positive λ-phage clone, a pBluescript SK-subclone was generated using the ExAssist™ phage system (Stratagene). The resulting clone was designated pPU3 and the *S. scabiei* cDNA insert was mapped for positions of restriction endonuclease cleavage using enzymes from Pharmacia Biotech (Uppsala, Sweden) and New England Biolabs. For the sequencing of pPU3, nested deletions and cDNA sequence specific primers were used in conjunction with the T7 sequence kit from Pharmacia Biotech.

Subcloning and Expression of MSA1

Construction of High Expression Vector

The open reading frame of the recombinant plasmid pPU3 was amplified by PCR using Pfu DNA polymerase (Stratagene) and subcloned into the XmnI-XbaI sites of the vector pPU16. The pPU16 vector is a derivative of the pMal-c2 vector (New England Biolabs) that has a sequence of DNA encoding for 6 consecutive histidine residues and a stop codon between the PstI and HindIII site. The resulting plasmid pPU17 encodes for the recombinant mite protein with the maltose binding protein fused to its N-terminus and a His6-tag fused to its C-terminus. The junction between the maltose binding protein and the recombinant mite protein has a factor Xa-binding site (IEGR).

Expression as Fused Protein The recombinant plasmid pPU17 was transformed into *E. coli* strain BL21 (DE3). The resulting transformant was inoculated into 10 ml minimal medium with casamino acids and heavy metals (MM/CA) (Pryor & Leiting, Protein Expr Purif 10:309) containing ampicillin (100 mg/ml) and grown overnight at 37° C. with continuous shaking. Five ml of the overnight culture was diluted in 500 ml fresh MM/CA medium with ampicillin (100 mg/ml) and grown in a 2-liter Ehrlenmeyer flask shaking efficiently at 37° C. until the OD value at 600 nm became 0.8. The culture was then cooled to 18° C., induced with 0.5 mM IPTG and then transffered to a shaker at 18° C. for continued growth for 20 h. After the expression the celles were collected by centrifugation at 4000×g for 20 min and resuspended in 25 ml 20 mM phosphate buffer (pH 7.6) with 0.5 M NaCl and 30 mM imidazole, supplemented with the Complete™ protease inhibitor (Roche) and frozen overnight at −70° C. The frozen cellsuspension was thawed in cold water, placed in an ice-water bath and sonicated. The suspension was clearified by centrifugation at 9000×g for 30 min and the resulting supernatant was used for affinity purification.

Minimal medium with casamino acids and heavy metal (MM/CA) is: 5 g/l glucose, 1 mg/l (+) biotin, 2 mg/l thiamine, 1 g/l $(NH_4)_2SO_4$, 4 ml of a 250× heavy metal stock solution, 50 ml sterile 10% casamino acids, and 200 ml sterile 5× phosphate buffer. One liter of 250× heavy metal stock solution is 500 mg $MoNa_2O_42H_2O$, 250 mg $CoCl_2$, 175 mg $CuSO_4$ $5H_2O$, 1 g $MnSO_4$ $H_2O$, 8.75 g $MgSO_47$ $H_2O$, 1.25 g $ZnSO_47$ $H_2O$, 1.25 g $FeCl_24$ $H_2O$, 2.5 g $CaCl_22$ $H_2O$, and 1.0 g $H_3BO_3$ in 1 M HCl. One liter of 5× phosphate buffer contains 53 g $K_2HPO_4$ and 24.7 g $KH_2PO_4$.

Purification of Recombinant Mite Antigen Fusion Protein

The supernatant was loaded onto a 1 ml HiTrap® chelating column (Amersham Pharmacia Biotech) loaded with $N^{2+}$ at a flow rate of 1 ml/min. After washing with 10 ml of 20 mM phospahate buffer (pH 7.6) with 0.5 M NaCl and 30 mM imidazole, the captured recombinant protein was eluted with 3 ml 20 mM phosphate buffer (pH 7.6) with 0.5 M NaCl and 500 mM imidazole. After buffer exchange to 20 mM Tris-HCl (pH 8.0) with 150 mM NaCl and 1 mM EDTA, the maltose binding protein was cleaved off with factor Xa at room temperature for 20 h after which the recombinant mite protein was purified on a HiTrap® column. As preserver Micro-O-Protect (Roche) was added to the purified recombinant protein in concentraion of 0.1%.

Cloning of Part of the 5' cDNA end of MSA1

A PCR strategy was used in order to clone regions upstream of the cDNA insert in pPU3. In the first PCR the primer KBE 5 (5'CAC TAT CGG AGA ACG TAA CTT CGG 3'), complementary to the anti-sense strand of the insert in pPU3, was desigend and used together with a T3 primer, complementary to the vector used to construct the cDNA library. As a template the *S. scabiei* cDNA-libray was used. The resulting fragment was cloned into the SmaI-site of pUC18 and sequenced as above. This new fragment was then used for the design of a second primer KBE 8 (5'CCT GGC ATT CTA CTT GAG ATG TA 3') for the amplification an additional 5'end cDNA fragment. The second 5'end fragment was cloned and sequenced as above. A continuos cDNA which included the original MSA1 cDNA and both of the 5' end fragments was generated by using the Titan™ One Tube RT-PCR system (manufactured by Roche). For the reverse transriptase step the reverse primer MSA1Xba (5'CGC TCT AGA CTC AAC AAT GAA TGT CTG CAA 3') was used. In the PCR, the reverse primer was used in combination with the forward primer LDL 2 (5'CGG GAT CCG AAT ATT TCG TCT CGA AAC CG 3'). The resulting fragment was cloned into the BamHI-XbaI sites of pPU16 utilizing the recognition sites introduced during the PCR (shown in boldface). A graphic overview of the cloning strategy is shown in FIG.

Enzyme-linked Immunosorbent Assay

The recombinant mite protein MSA1 was diluted in a 0.1 M carbonate buffer, pH 9.6, to a concentration of 62.5 ng/ml and coated overnight at 4° C. onto microtitre plates (Polysorp, manufactured by Nunc) in volumes of 100 μl per well. The plates was washed once with phospate buffered saline with 0.05% Tween20 (PBS-T) followed by the addition of serum samples at a 1:100 dilution in PBS-T. After a 1 h incubation at 37° C. the plates were washed three times with PBS-T and a monclonal mouse anti-dog IgG antibody, dilution 1:1000, and rabbit anti-mouse Ig conjugated to HRP (manufactured by Dako), dilution 1:1000, in PBS-T plus 1% normal rabbit serum were added to the wells and incubated for 1 h at 37° C. After washing three times with PBS-T, 100 μl of TMB (manufactured by Sigma) were added to each well. The substrate incubation was stopped with 50 μl of $H_2SO_4$ and the amount of end product was analyzed at 450 nm in Dynatech MR5000 spectrophotometer (manufactured by Dynatech).

Affinity Puriciation of Antibodies

Purified recombinant mite protein or recombinant phages in *E. coli* expressing the recombinant mite protein were transferred to a nitro cellulose filter. After blocking the filter with 1% BSA (Strategene) in 20 mM Tris-HCl, 0.5 M NaCl, 0.05% Tween20, pH 7.5 (TTBS), anti-*S. scabiei* rabbit serum was added to the filter and incubated for 1 h at room temperature. After extensive washing with TTBS, the bound antibodies were eluted and used in Western blot analysis on *S. scabiei* antigens(Beall & Mitchell, J. Immunol. Method. (1986) 86:217). The affinity purfied antibodies were also used to localize the protein in *S. scabiei* mites.

Western Blot Analysis

Purified recombinant mite proteins were separated by SDS-PAGE in 12% mini gels in Mini PROTEAN II cell (Bio-Rad Laboratories). Blotting of proteins to nitrocellulose was done by using an electrophoretic transfer cell (Bio-Rad Laboratories). After completion of transfer, the membrane bound proteins were checked by briefly incubating the membrane in a 0.2% Ponceau-S solution (Sigma) followed by rinsing in distilled water. The blots were blocked with phosphate buffer saline (PBS) containing nonfat dry milk, incubated with sera from experimentally dogs (Bornstein & Zakrisson (1993) *Vet. Dermatol.* 4:107), then incubated with a mouse anti-dog IgG monoclonal antibody and a rabbit anti-mouse IgG. After washing, bound antibodies were visualized by chemiluminescence detection and exposure to film using the ECL-system (Amersham Pharmacia Biotech).

The invention claimed is:

1. An immunogenic preparation comprising a protein consisting of amino acids 1–83 of SEQ ID. NO. 2 and a pharmaceutically and/or veterinary acceptable carrier.

2. The immunogenic preparation according to claim 1, wherein said immunogenic preparation is in a unit dosage form.

3. A peptide consisting of amino acids 1–83 of SEQ ID NO. 2.

* * * * *